(12) United States Patent
Kondo et al.

(10) Patent No.: US 11,464,733 B2
(45) Date of Patent: *Oct. 11, 2022

(54) ENEMA FOR RECTAL APPLICATION

(71) Applicant: Dr. Falk Pharma GmbH, Freiburg (DE)

(72) Inventors: Shoji Kondo, Tokyo (JP); Morio Iwasaki, Tokyo (JP); Yoji Yamada, Tokyo (JP)

(73) Assignee: DR. FALK PHARMA GMBH, Freiburg (DE)

( * ) Notice: Subject to any disclaimer, the term of this patent is extended or adjusted under 35 U.S.C. 154(b) by 358 days.

This patent is subject to a terminal disclaimer.

(21) Appl. No.: 16/472,490

(22) PCT Filed: Dec. 21, 2017

(86) PCT No.: PCT/EP2017/083995
§ 371 (c)(1),
(2) Date: Jun. 21, 2019

(87) PCT Pub. No.: WO2018/122086
PCT Pub. Date: Jul. 5, 2018

(65) Prior Publication Data
US 2021/0128456 A1 May 6, 2021

(30) Foreign Application Priority Data
Dec. 28, 2016 (JP) .............................. JP2016-254999

(51) Int. Cl.
| | | |
|---|---|---|
| *A61P 1/04* | (2006.01) | |
| *A61K 9/02* | (2006.01) | |
| *A61K 9/12* | (2006.01) | |
| *A61K 31/58* | (2006.01) | |
| *A61K 9/00* | (2006.01) | |

(52) U.S. Cl.
CPC .............. *A61K 9/0031* (2013.01); *A61K 9/02* (2013.01); *A61K 9/12* (2013.01); *A61K 31/58* (2013.01); *A61P 1/04* (2018.01)

(58) Field of Classification Search
None
See application file for complete search history.

(56) References Cited

U.S. PATENT DOCUMENTS

| | | | |
|---|---|---|---|
| 5,914,122 A | 6/1999 | Otterbeck et al. | |
| 8,476,233 B2 * | 7/2013 | Pravda | A61P 43/00 |
| | | | 514/13.2 |
| 8,916,546 B2 * | 12/2014 | Pravda | A61K 31/616 |
| | | | 514/183 |
| 2014/0135299 A1 * | 5/2014 | Palepu | A61K 31/353 |
| | | | 514/171 |
| 2014/0349982 A1 | 11/2014 | Forbes et al. | |
| 2018/0271786 A1 | 9/2018 | Yamada et al. | |

FOREIGN PATENT DOCUMENTS

| | | |
|---|---|---|
| WO | WO 2014/189955 A1 | 11/2014 |
| WO | WO 2016/121147 A1 | 8/2016 |

OTHER PUBLICATIONS

Hanauer et al., Budesonide enema for the treatment of active, distal ulcerative colitis and proctitis: a dose-ranging study, (115, No. 3, 525-32, 1998) 4 Fig. 4 Tab. 19 Ref (Year: 1998).*
Greenberg et al., Oral budesonidc for active Crohn's disease, N Engl J Med 1994;33 I :836-4 I. (Year: 1994).*
International Search Report in PCT/EP2017/083995, dated May 8, 2018.
International Witten Opinion in PCT/EP2017/083995, dated May 8, 2018.
Anonymous, "Public Assessment Report of the Medicines Evaluation Board in the Netherlands: Budenofalk Schuim 2 mg, rectal foam", College ter Beoordeling van Geneesmiddelen—Medicines Information Bank, Dec. 6, 2012.
Mikihiro Fuji Ya, Yutaka Kogo, "Mucosal healing in ulcerative colitis," The Japanese Journal of Gastro-enterology, 2013, vol. 110, pp. 1900 to 1908, table 2.
Lindgren et al., "Effect of Budesonide Enema on 1-6 Remission and Relapse Rate in Distal Ulcerative Colitis and Proctitis", Scand. J. Gastroenterol., 2002, vol. 37, No. 6, pp. 705-710.
Naganuma et al., "Twice-daily Budesonide 2-mg Foam Induces Complete Mucosal Healing in Patients with Distal Ulcerative Colitis", Journal of Crohn's and Colitis, vol. 10, No. 7, pp. 828-836, Nov. 16, 2015.

* cited by examiner

*Primary Examiner* — Alton N Pryor
(74) *Attorney, Agent, or Firm* — Curatolo Sidoti & Trillis Co., LPA; Salvatore A Sidoti; Floyd Trillis, III

(57) ABSTRACT

Provided is an enema for rectal application containing budesonide as an active ingredient in order to treat an inflammatory bowel disease, or to prevent a relapse.
The enema for rectal application contains budesonide as the active ingredient, in which 1.5 to 2.5 mg of budesonide per dose is administered twice a day for 12 weeks in order to treat an inflammatory bowel disease, or to prevent a relapse. The enema for rectal application comprises several doses whereby the most preferable dose of budesonide is 2.0 mg per dose. The enema for rectal application is taken in order to treat ulcerative colitis or Crohn's disease, or to prevent a relapse; has a foamy, more rigid to a more liquid, gel-like structure.

2 Claims, No Drawings

ENEMA FOR RECTAL APPLICATION

CROSS REFERENCE TO RELATED APPLICATIONS

This application is a national stage application under 35 U.S.C. § 371 of International Application No. PCT/EP2017/083995, filed 21 Dec. 2017, which claims priority from Japanese Patent Application No. 2016-254999, filed 28 Dec. 2016, which applications are hereby incorporated herein by reference in their entireties.

TECHNICAL FIELD

The present invention relates to an enema for rectal application containing budesonide as an active ingredient in order to treat an inflammatory bowel disease, or to prevent a relapse.

BACKGROUND ART

Ulcerative colitis is a nonspecific inflammatory bowel disease of unknown cause that can cause ulcers and erosion mainly in a large intestine mucosa, and Crohn's disease is an inflammatory bowel disease of unknown cause which causes a discontinuous chronic granulomatous inflammation mainly in an entire digestive tract from an oral cavity to an anus. In any case, bloody stool, mucous and bloody stool, diarrhea, abdominal pain, and the like are common symptoms, and when the symptoms become severe, general social life is interfered with. In addition, curative treatment is not established for these, and thus once these develop, these will repeat relapse and remission. Therefore, in order to improve the quality of life (QOL) of patients, it is important to maintain the remission period as long as possible.

Generally, medication treatment is done for the purpose of leading to clinical remission. Therefore, for example, in the ulcerative colitis, in a case where the clinical symptoms disappear or are improved to the extent that the symptoms do not interfere with daily life, such as bloody stools disappear and a defecation frequency decreases to the extent that the defecation does not interfere with the daily life, even in a case where mucosal inflammation of the intestinal tract is not completely disappeared and mild inflammation is confirmed, it is said to be remission. However, in recent years, it is reported that in patient group with intestinal mucosa recovered normally (mucosal healing is reached), prognosis is good for a long period of time, and remission maintenance is significantly improved as compared with a patient group who has redness in intestinal mucosa or decreased vascular permeability, at the end of medication treatment (for example, refer to Non-Patent Documents 1 and 2.) That is, in order to maintain the remission period as long as possible, it is important to aim not only clinical remission, but also intestinal mucosal healing, at the time of treatment in active phase.

Budesonide ((+)-[(RS)-16α,17α-Butylidenedioxy-11β,21-dihydroxy-1,4-pregnadiene-3,20-dione]) is a steroid drug applied as a therapeutic agent for the inflammatory bowel diseases such as the ulcerative colitis and the Crohn's disease. Budesonide is effective for topical administration and is generally used as an enema for rectal application for pharmaceutical foams and enema agents packed with compressed gas (refer to Patent Document 1). For treatment of the ulcerative colitis and the like, generally, 2 mg of budesonide is administered once a day for 6 weeks. In addition, in a patient group of the ulcerative colitis, in which 2 mg of budesonide is administered twice a day (dose per day is 4 mg) for 2 weeks and then 2 mg of budesonide is administered once a day for 4 weeks, it is reported that the effect of improving a modified Mayo Disease Activity Index (MM-DAI) to 0 or 1 is significantly higher than a placebo administered group (refer to Patent Document 2).

Further, it is also reported that the healing effect of large intestine mucosa is highly intentional in the ulcerative colitis patients who administered 2 mg of budesonide twice a day for 6 weeks, compared with the ulcerative colitis patients who administered 2 mg of budesonide once a day for 6 weeks (refer to Patent Document 3).

CITATION LIST

Patent Literature

[Patent Document 1] JP Patent Publication No. 3421348
[Patent Document 2] United States Patent Application, Publication No. 2014/0349982
[Patent Document 3] International Publication No. WO 2016/121147

Non-Patent Literature

[Non-Patent Document 1] Colombel, et al., GASTROENTEROLOGY, 2011, vol. 141, p. 1194-1201.
[Non-Patent Document 2] Yokoyama, et al., Gastroenterology Research and Practice, 2013, vol. 2013, Article ID 192794.

SUMMARY OF THE INVENTION

Technical Problem

An object of the present invention is to provide an enema for rectal application in which the mucosal healing effect is significantly superior to an enema of the related art, in an enema for rectal application containing budesonide as an active ingredient in order to treat an inflammatory bowel disease, or to prevent a relapse.

Solution to Problem

As a result of intensive studies to solve the above problems, the present inventors found that the patient's percentage of mucosal healing without severe side effects was significantly higher as compared with the placebo group, when an enema for rectal application with budesonide as an active ingredient was administered twice a day for an additional 6 weeks to patients who have been administered an enema for rectal application with budesonide as an active ingredient twice a day for six weeks who have shown some signs of healing (an endoscope view score of 1 point) but no mucous membrane healing (an endoscope view score of 0 points), and thus completed the present invention.

That is, embodiments of the present invention relate to an enema for rectal application of the following points [1] to [7].

[1] An enema for rectal application containing budesonide as an active ingredient, in which 1.5 to 2.5 mg of budesonide per dose is administered twice a day for 6 weeks in order to treat an inflammatory bowel disease, or to prevent a relapse.
[2] The enema for rectal application according to the above [1], in which a dose of budesonide is 2.0 mg per dose.

[3] The enema for rectal application according to the above [1] or [2], which is administered in order to treat ulcerative colitis or Crohn's disease, or to prevent a relapse.
[4] The enema for rectal application according to any one of the above [1] to [3], which has a foamy shape or a liquid shape. Foamy shape means a stiffer and somewhat rigid structure whereas liquid shape means a softer, gel-like structure.
[5] A package of an enema for rectal application, in which the enema for rectal application according to any one of the above [1] to [4], for additionally administering 1.5 to 2.5 mg of budesonide twice a day for an additional 6 weeks to a patient with inflammatory bowel disease who has been administered 1.5 to 2.5 mg of budesonide twice a day for 6 weeks and has shown some signs of healing but no mucous membrane healing (an endoscope view score of 0 points).
[6] A package of an enema for rectal application, in which the enema for rectal application according to any one of the above [1] to [5] contains 1.5 to 2.5 mg of budesonide per dose can be administered 14 times.
[7] A manufacturing method of a package of an enema for rectal application, in which the enema for rectal application according to any one of the above [1] to [5] is adjusted such that the enema for rectal application containing 1.5 to 2.5 mg of budesonide per dose can be administered 14 times.

Advantageous Effects of Invention

The enema for rectal application according to the present invention has remarkably high healing effect on intestinal mucosa where ulcer and erosion occur due to inflammation. Therefore, the enema for rectal application according to the present invention is extremely excellent as an enema for rectal application in order to treat the inflammatory bowel disease such as ulcerative colitis and Crohn's disease or the like, or to prevent a relapse.

DESCRIPTION OF EMBODIMENTS

Hereinafter, the present invention will be described in detail by showing embodiments. An enema for rectal application according to the present embodiment is administered (taken) with budesonide as an active ingredient, and 1.5 to 2.5 mg of budesonide twice a day for 6 weeks in order to treat an inflammatory bowel disease, or to prevent a relapse. In the related art, budesonide is used as a therapeutic agent for the inflammatory bowel disease by administering 2 mg once a day for 6 weeks directly to the rectum. On the contrary, although the dose per day of the enema for rectal application according to the present embodiment are the same as those of the method of the related art, the effect of healing an inflammation of an intestinal mucosa is significantly superior to the case of taking once a day in the related art. In addition, the administration period of the enema for rectal application according to the present embodiment is 12 weeks, which is twice as much as the administration period as that of the method of the related art, and the longer administration period can increase the percentage of healing intestinal mucosa for inflammatory bowel disease patients that cannot be cured with an administration period of 6 weeks. Furthermore, in order to obtain a sufficient effect, it is preferable to take doses twice a day for 12 weeks. That is, the administration period can be selected from more than 6 weeks and not more than 12 weeks, and is preferably 12 weeks. Here, the week means an approximate period, and even if the administration period increases or decreases for several days due to convenience of administration to an inflammatory bowel disease patient, the effect can be obtained, so that the administration period includes approximately ±3 days as a guidance. In the present specification, although taking the dose widely refers to administration to the inflammatory bowel disease patient, in the embodiment as described later, a method of transanal administration by suppository or the like is included.

The administration period of the enema for rectal application according to the present embodiment is twice that of methods in the related art, and the enema can be safely taken as much as the method of the related art without any special side effects when compared thereto. Although the enema for rectal application according to the present embodiment is a local administration agent, the active ingredient budesonide is a steroid, and the administration period is limited within 6 weeks in the related art. It has been newly discovered that taking the enema of the present invention for over six weeks can be relatively safe.

Budesonide has two diastereomers of 22R and 22S. The active ingredient of the enema for rectal application according to the present embodiment may be any one of these diastereomers or may be a mixture thereof (for example, a racemate containing approximately equal amounts of both diastereomers). In several pharmacological aspects, since 22R of the two diastereomers of budesonide is more active than 22S, as the active ingredient of the enema for rectal application according to the embodiment, it is preferable to use racemic or 22R diastereomer, and more preferably 22R diastereomer.

Although the enema for rectal application according to the present embodiment is taken twice a day, and the time point of taking the dose within one day is not particularly limited, it is preferable to have an interval at least 6 hours or more and less than one day (24 hours), and more preferable to take in the morning and night. In addition, as much as possible, it is preferable taken after defecation.

In the enema for rectal application according to the present embodiment, it is preferable to take budesonide twice a day for adults within the range of 1.5 to 2.5 mg per dose, and particularly preferable to take budesonide twice a day at 2 mg per dose.

In a case where the enema for rectal application according to the embodiment is a liquid agent, since the stability of budesonide is high, the pH of the liquid agent is preferably 6.0 or less, more preferably 3.0 to 6.0 from the viewpoint of physiological tolerability, and still more preferably 3.5 to 6.0.

In addition, since budesonide has low solubility in water, in a case where the enema for rectal application according to the embodiment is the liquid agent, solvent for dissolving budesonide is preferably an alcohol or a mixed solvent of water and alcohol. Examples of the alcohols include propylene glycol, ethanol, isopropanol, and the like. The alcohol used as the solvent may be only one type, or two types or more of alcohols may be used in mixture. In a case where the mixed solvent of water and alcohol is used, the ratio of alcohols to water is preferably 100:0 to 80:20, more preferably 98:2 to 93:7, in the mass ratio of water:alcohol. The nature of the ethanol has to be taken into account since for example a high concentration of ethanol may not be desirable.

Since the stability of budesonide can be improved, the enema for rectal application according to the present embodiment preferably contains EDTA sodium salt (sodium ethylenediaminetetraacetate) and/or cyclodextrins. As cyclodextrins, β-cyclodextrin, hydroxy-β-cyclodextrin, or γ-cyclodextrin is preferable.

In addition to the above, the enema for rectal application according to the embodiment may contain various pharmaceutically acceptable additives according to the requirements of the preparation. Examples of such additives include pH adjusters (buffer), preservatives, thickeners, emulsifiers, and the like. Examples of the pH adjuster (buffer) include acids such as acetic acid, citric acid, tartaric acid, hydrochloric acid, phosphoric acid and the like; bases such as potassium hydroxide or sodium hydroxide; or a buffer solution such as a hydrochloric acid buffer solution, a phthalate buffer solution, a phosphate buffer solution, a borate buffer solution, an acetate buffer solution or a citrate buffer solution, and the like. Examples of the preservatives include ethanol, chlorobutanol, benzyl alcohol, phenylethanol, sorbic acid, benzoic acid, sodium disulfite, p-hydroxybenzoate, phenol, m-cresol, p-chloro-m-cresol, a quaternary ammonium salt, or a chlorhexidine, and the like. Examples of the thickener include gelatin, tragacanth, pectin, cellulose derivatives (for example, methyl cellulose, hydroxypropyl methyl cellulose, carboxymethyl cellulose sodium, and the like), polyvinylpyrrolidone, polyvinyl alcohol, polyacrylic acids, xanthan gum, or xanthan gum, and the like. Examples of the emulsifier include aliphatic alcohols such as cetearyl alcohol, cetyl alcohol, stearyl alcohol or myristyl alcohol; and polyoxyethylene alkyl ethers such as polyoxyethylene cetostearyl ether or polyoxyethylene lauryl ether, and the like.

The dosage form of the enema for rectal application according to the present embodiment is not particularly limited as long as the enema is administered transanal directly into the intestinal tract. In the embodiment, the enema for rectal application in the form of a foamy shape or a liquid shape can be used, and examples thereof include a rectal foaming agent, an enema agent, a suppository, and the like. The enema agent may be one that can be distributed as a liquid agent or may be prepared by dissolving a tablet containing budesonide in a solvent such as water just before taking. As the enema for rectal application according to the embodiment, a rectal foaming agent or an enema agent is preferable, and the rectal foaming agent is particularly preferable, since the enema can be directly administered into the large intestine from the anus. Here, the foaming agent refers to a mode in which bubbles are formed by an aqueous solution of the liquid agent to form the foams of aggregated bubbles, and the like. The foaming agent is administered by spraying the foam or the like, on the inflammatory bowel disease patient.

The rectal foaming agent, the enema agent, and the suppository containing budesonide as the active ingredient can be prepared by a known method of the related art, except that these are manufactured so that the dose of budesonide is 1.5 to 2.5 mg per dose. Compositions for the treatment or the prevention of relapse of the inflammatory bowel disease containing budesonide and the other ingredients described above can be adjusted to the form of the various enemas for rectal application described above. For example, the rectal foaming agent and the enema agent containing budesonide as the active ingredient can be manufactured by the method described in Patent Document 1. For example, the rectal foaming agent containing budesonide as the active ingredient can be manufactured as follows. Budesonide dissolved in alcohol is added to the solution prepared by dissolving a preservative or an emulsifier necessary for foam formation in a mixed solvent of alcohols or water and alcohols, and mixed. Thereafter, an aqueous solution in which EDTA sodium salt and an acid are dissolved is stirred while homogenizing. The obtained solution is sealed in a gas filling pack equipped with a commercial valve system as a device for single or multiple administrations, and subsequently propellant gas is added. As the propellant gas, hydrocarbons such as isobutane, n-butane or propane/n-butane mixture are preferable. The gas filling pack may further be provided with a plastic applicator chip.

The enema for rectal application according to the present embodiment may be provided for each medicine package of a single dose, but it may be provided by appropriately adjusting the form that is easy to administer twice a day for 12 weeks. For example, an enema foaming agent can be provided by packing the amount of 14 doses comprising a foaming agent (for one week) in aluminum cans, or packaging the dosages for 2 weeks (dosages for 28 times) in aluminum cans (aerosol). In addition, these may be combined for 6 to 12 weeks. Such packages are easy to be used appropriately for prescription for one person.

Since the enema for rectal application according to the embodiment is excellent in the healing effect of the intestinal mucosa, it is preferably used in order to treat an inflammatory bowel disease, or to prevent a relapse. Among these, it is preferable to take the enema in order to treat ulcerative colitis or Crohn's disease, or to prevent a relapse. It is more preferable to take the enema in order to treat the ulcerative colitis or the Crohn's disease in which there is a lesion from a rectum to a sigmoid colon, or to prevent the relapse. It is preferable, for patients with inflammatory bowel disease who have been administered 1.5 to 2.5 mg of budesonide twice a day for 6 weeks and have been shown some signs of healing but no mucous membrane healing (an endoscope view score of 0 points), to administer 1.5 to 2.5 mg of budesonide twice a day for an additional 6 weeks. By continuing to administer budesonide twice a day beyond the conventional administration period of 6 weeks, healing effects can be gained for patients of the inflammatory bowel disease who did not experience mucous membrane healing with an administration period of 6 weeks.

Furthermore, the treatment in the embodiment widely refers to improvement of the symptoms of patients of inflammatory bowel disease. The prevention of relapse in the embodiment widely refers to prevent symptom deterioration (relapse) of the symptoms of the disease completely or to some extent for the patients of inflammatory bowel disease after improvement. Since inflammation of the mucosa can be further improved by taking the enema for rectal application according to the embodiment than the method of the related art of taking budesonide once a day, it can be expected that patients taking the enema for rectal application according to the embodiment can maintain remission for a longer period of time after administration. In addition, the enema for rectal application according to the embodiment may be taken in order to treat pouchitis which is an inflammation occurring in the ileac pouch (formed in a pouch shape) after total colonic removal of ulcerative colitis, or to prevent a relapse, similarly to budesonide enema of the related art for rectal application (Gionchetti et al., Alimentary Pharmacology & Therapeutics, 2007, vol. 25, p. 1231-1236; Sambuelli et al., Alimentary Pharmacology & Therapeutics, 2002, vol. 16, p. 27-34).

EXAMPLES

Next, the present embodiment will be described in more detail by showing an application example, and the like, but the present invention will not be limited thereto.

Application Example 1

Placebo-controlled randomized double-blind multicenter collaborative parallel group comparison test Superiority of the budesonide compared with placebo for mucosal healing as the primary endpoint are investigated for patients with active ulcerative colitis when budesonide 2 mg is rectally administered twice a day for 6 weeks by a double-blind comparative study with placebo as a control, and the safety thereof was investigated.

Furthermore, the efficacy and safety of administering were investigated, to patients with inflammatory bowel disease who have been administered 1.5 to 2.5 mg of budesonide twice a day for 6 weeks and shown signs of healing but no mucous membrane healing, 1.5 to 2.5 mg of budesonide twice a day for an additional 6 weeks (for a total of 12 weeks) (clinical trial number: Japic CTI—142704).

This clinical trial is conducted in compliance with the ethical principles based on the "Declaration of Helsinki" and the criteria prescribed in Article 14, paragraph 3 and Article 80, paragraph 2 of the Pharmaceutical Affairs Law, and "Standards for Implementation of Clinical Trials for Pharmaceuticals (GCP)". In addition, prior to the implementation of the clinical trial, ethical, scientific, medical and pharmacological validity of this clinical trial is examined and approved by the clinical trial review committee.

<Test Drug and Control Drug>

For the trial, an aerosol with fixed dose injection type for rectal injection (rectal foaming agent) is used as a test drug, in which 25 mL (1.35 g) of white creamy foam containing 2 mg of budesonide is released by one injection. As a remission induction therapeutic agent of ulcerative colitis in active phase where the lesion is confined to the rectum and sigmoid colon, the aerosol for rectal injection is approved in Europe at a dosage and dose of budesonide 2 mg once a day (trade name: Budenofalk 2 mg/dose rectal foam, manufactured by Dr. Falk Pharma GmbH).

In addition, as a control drug, an aerosol with fixed dose injection type for rectal injection, of which the appearance and weight, and the like are indistinguishable from the test drug, and which does not contain budesonide, is used.

<Subjects>

The subjects are ulcerative colitis patients in active phase, and are divided into a group administered the test drug twice a day (hereafter, the budesonide-administered group), and a group administered the control drug (hereinafter, the placebo group).

<Dose, Administration Method and Administration Period>

The test drug or control drug is rectally administered twice a day (once in the morning and once in the evening), after defecation, if possible. The number of injections per dose is one, the administration period is 6 weeks, if no mucous membrane healing occurred (an endoscope view score of 0 points), an administration period of 12 weeks can be used, and the drug is administered until the evening before the evaluation. The dose of budesonide in each group is 4 mg/day for the twice a day group, and 0 mg/day for the placebo group. The subjects with a 12-week administration period included 20 subjects in the budesonide administered group, and 18 subjects in the placebo group.

<Results>

Each subject was subjected to mucosal endoscopy before administration (week 0), week 6, and week 12, and the MMDAI endoscopic finding score (0=normal or inactive findings, 1=mild (redness, decreased vascular permeability), 2=moderate (significant redness, disappearance of vascular permeability, fragility, erosion), 3=severe (spontaneous bleeding, ulcer)) of 1 or less are investigated. Judgment of the endoscopic finding score resulted in two scores, the score by the doctor in attendance, and the score by the central judgment committee. The score by the doctor was used for the initial test, and after an administration period of 6 weeks, whether the prescription was continued for 6 more weeks or not. The score by the central judgment committee was used as the judgement of effectiveness. The endoscopic finding score shown in Tables 1 to 3 shows the value by the central judgment committee. The measurement result of subjects who had been administered to for 12 weeks is shown in Table 1. Furthermore, the change of the endoscope finding score from 6th week to 12th week of each subject of placebo group is shown in Table 2, and the change in the endoscope finding score from 6th week to 12th week of each subject of the budesonide-administered group is shown in Table 3.

TABLE 1

| Judged period | Administered Group | | Placebo group | Budesonide-administered group |
|---|---|---|---|---|
| 0 week | Analysis target case | | 18 | 20 |
| | Score | 0 | 0 (0.0) | 0 (0.0) |
| | | 1 | 4 (22.2) | 3 (15.0) |
| | | 2 | 13 (72.2) | 16 (80.0) |
| | | 3 | 1 (5.6) | 1 (5.0) |
| 6th week | Analysis target case | | 18 | 20 |
| | Score | 0 | 0 (0.0) | 4 (20.0) |
| | | 1 | 14 (77.8) | 14 (70.0) |
| | | 2 | 4 (22.2) | 2 (10.0) |
| | | 3 | 0 (0.0) | 0 (0.0) |
| 12th week | Analysis target case | | 18 | 20 |
| | Score | 0 | 0 (0.0) | 6 (30.0) |
| | | 1 | 11 (61.1) | 8 (40.0) |
| | | 2 | 7 (38.9) | 6 (30.0) |
| | | 3 | 0 (0.0) | 0 (0.0) |

As shown in Table 1, there was a decrease in the scores of both of the two groups in both the 6th week or 12th week, and the size of the decrease of the score which indicates an improvement of the mucous membrane in the budesonide treatment group is large compared with that of the placebo group.

TABLE 2

| | | 6th week | | | | |
|---|---|---|---|---|---|---|
| Placebo group | | 0 | 1 | 2 | 3 | Total |
| 12th week | 0 | 0 (0.0) | 0 (0.0) | 0 (0.0) | 0 (0.0) | 0 (0.0) |
| | 1 | 0 (0.0) | 8 (44.4) | 2 (11.1) | 0 (0.0) | 10 (55.6) |
| | 2 | 0 (0.0) | 2 (11.1) | 1 (5.6) | 0 (0.0) | 3 (16.7) |
| | 3 | 0 (0.0) | 0 (0.0) | 0 (0.0) | 0 (0.0) | 0 (0.0) |
| | Unmeasured | 0 (0.0) | 4 (22.2) | 1 (5.6) | 0 (0.0) | 5 (27.8) |
| | Total | 0 (0.0) | 14 (77.8) | 4 (22.2) | 0 (0.0) | 18 (100.0) |

TABLE 3

| Budesonide group | | 6th week | | | | |
|---|---|---|---|---|---|---|
| | | 0 | 1 | 2 | 3 | Total |
| 12th week | 0 | 0 (0.0) | 5 (25.0) | 1 (5.0) | 0 (0.0) | 6 (30.0) |
| | 1 | 1 (5.0) | 6 (30.0) | 0 (0.0) | 0 (0.0) | 7 (35.0) |
| | 2 | 0 (0.0) | 1 (5.0) | 1 (5.0) | 0 (0.0) | 2 (10.0) |
| | 3 | 0 (0.0) | 0 (0.0) | 0 (0.0) | 0 (0.0) | 0 (0.0) |
| | Unmeasured | 3 (15.0) | 2 (10.0) | 0 (0.0) | 0 (0.0) | 5 (25.0) |
| Total | | 4 (20.0) | 14 (70.0) | 2 (10.0) | 0 (0.0) | 20 (100.0) |

As shown in Table 2, in placebo group, none of the subjects had improved enough to have an endoscope view score of 0. On the other hand, in the Budesonide treatment group, the score of 1/20 subjects (5.0%) changed from 0 to 1, the score of 5/20 subjects (25.0%) changed from 1 to 0, the score of 1/20 subjects (5.0%) changed from 1 to 2, the score of 1/20 subjects (5.0%) changed from 2 to 0, and the subjects of endoscope view score 0 in the 12th week include 5 subjects who changed from 1 to 1 in the 6th week, and 1 subject who changed from 2 to 0, for a total of 6 subjects (40.0%) with a score of zero. In other words, as a result of the continued for 6 weeks administration of a test drug to the subjects of endoscope view score 1 in the 6th week, the percentage with an endoscope view score of 0 in the 12th week, except for non-measured group, of the Budesonide administration group was 40.0% (6/15 examples), compared to the percentage of the placebo group 0% (0/13 examples), and clearly the Budesonide administration group was superior with the placebo group.

From the results, it is clear, for patients with inflammatory bowel disease who have been administered an enema for rectal application including budesonide as an active ingredient twice a day for 6 weeks and shown some signs of healing but no mucous membrane healing, that an additional administration twice a day for a further 6 weeks showed a therapeutic effect and significantly improved mucous membrane healing.

On the other hand, regarding safety, the manifested frequency of the adverse event in Budesonide treatment group was higher than in the placebo group; however, manifestation of adverse events as a result of the drug tested couldn't admit between Placebo group.

Furthermore, no death, severe adverse events or serious adverse event, were observed in the 12 week administration of the test drug.

Hematology checks and blood biochemistry checks were performed, and the serous cortisol density (concentration of cortisol in serum or plasma cortisol) in the 6th week and the 12th week in budesonide treatment group were low compared with the 0th week (before prescription); however, the subjects were observed for 2-4 weeks after the end of the 12-week administration period, and by the end, the serous cortisol density was reverting to the value in the 0th week. Furthermore, in the Budesonide treatment group, a decrease of the percentage of the acidophilic leucocyte of leukocyte fractionation could be observed from the 4th week to the 12th week compared with the 0th week and placebo group, but no clear fluctuation in other items could be seen. Table 4 shows the percentage of cases below a standard value in terms of serous cortisol density and serous ACTH (adrenocorticotropic hormone) density in the 0th week of budesonide treatment group and placebo group (before prescription), in the 12th week (prescription end), and in the time after observation.

TABLE 4

| Judgement timing | Dosed group | Placebo Group | Budesonide treatment group | Total |
|---|---|---|---|---|
| Serous cortisol | | | | |
| 0th week | Number of cases for Analysis | 18 | 20 | 38 |
| | Applicable example | 0 | 0 | 0 |
| | Percentage (%) | 0.0 | 0.0 | 0.0 |
| 12th week | Number of cases for Analysis | 18 | 19 | 37 |
| | Applicable example | 1 | 11 | 12 |
| | Percentage (%) | 5.6 | 57.9 | 32.4 |
| After observation | Number of cases for Analysis | 16 | 20 | 36 |
| | Applicable example | 0 | 2 | 2 |
| | Percentage (%) | 0.0 | 10.0 | 5.6 |
| Serous ACTH | | | | |
| 0th week | Number of cases for Analysis | 18 | 20 | 38 |
| | Applicable example | 0 | 3 | 3 |
| | Percentage (%) | 0.0 | 15.0 | 7.9 |
| 12th week | Number of cases for Analysis | 18 | 19 | 37 |
| | Applicable example | 0 | 8 | 8 |
| | Percentage (%) | 0.0 | 42.1 | 21.6 |
| After observation | Number of cases for Analysis | 16 | 20 | 36 |
| | Applicable example | 0 | 2 | 2 |
| | Percentage (%) | 0.0 | 10.0 | 5.6 |

As shown in Table 4, the number of cases below standard value of plasma levels, for the 0th week, for the 12th week, and for the time after observation, are, respectively, placebo group 0% (0/18 examples), 5.6% (1/18 examples), and 0% (0/16 examples) for the placebo group, and 0% (0/20 examples), 57.9% (11/19 examples) and 10.0% for the budesonide treatment group. In addition, the number of cases with a standard value of serous ATCH density are, respectively, 0% (0/18 examples), 0% (0/18 examples), 0% (0/16 examples) for the placebo group, and 15.0% (3/20 examples), 42.1% (8/19 examples) and 10.0% (2/20 examples) for the budesonide treatment group. In addition, the subjects with both a serous cortisol density and a serous ACTH density in the 12th week below the standard value, mostly recovered to within the standard value by the after observation. Furthermore, in the administration period for 12 weeks and in an observation period after prescription, an increase in the incidence of adverse events related to side reaction of glucocorticoids was not observed. From these results, it is considered that tolerability of budesonide 2 mg to patients of ulcerative colitis for rectal administration twice a day for 6 weeks is acceptable.

INDUSTRIAL APPLICABILITY

The enema for rectal application according to the present invention has remarkably high healing effect on intestinal mucosa where ulcer and erosion occur due to inflammation. Therefore, the enema for rectal application according to the present invention is extremely useful as an enema for rectal application in order to treat the inflammatory bowel disease such as ulcerative colitis and Crohn's disease or the like, or to prevent a relapse.

The invention claimed is:

1. A method of preventing relapse of inflammatory bowel disease by transanally administering an enema comprising 1.5 to 2.5 mg of budesonide twice a day for 12 weeks, wherein when administering twice a day, the enema is administered twice after an interval of 6 hours or more.

2. A method of healing intestinal mucosa caused by inflammatory bowel disease by transanally administering an enema comprising 1.5 to 2.5 mg of budesonide twice a day for 12 weeks, wherein when administering twice a day, the enema is administered twice after an interval of 6 hours or more.

* * * * *